US011225517B2

(12) United States Patent
Giamarellos-Bourboulis et al.

(10) Patent No.: US 11,225,517 B2
(45) Date of Patent: Jan. 18, 2022

(54) TREATMENT OF HIDRADENITIS SUPPURATIVA

(71) Applicant: Janssen Biotech, Inc., Horsham, PA (US)

(72) Inventors: Evangelos J. Giamarellos-Bourboulis, Athens (GR); Stanley A. Kim, Naples, FL (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/899,864

(22) Filed: Feb. 20, 2018

(65) Prior Publication Data

US 2018/0230211 A1    Aug. 16, 2018

Related U.S. Application Data

(63) Continuation of application No. PCT/IB2018/000209, filed on Feb. 16, 2018.

(60) Provisional application No. 62/459,841, filed on Feb. 16, 2017.

(51) Int. Cl.
| A61K 39/00 | (2006.01) |
| C07K 16/24 | (2006.01) |
| A61P 17/00 | (2006.01) |
| C07K 16/12 | (2006.01) |

(52) U.S. Cl.
CPC ............ *C07K 16/245* (2013.01); *A61P 17/00* (2018.01); *C07K 16/1271* (2013.01); *A61K 2039/505* (2013.01); *A61K 2039/507* (2013.01)

(58) Field of Classification Search
None
See application file for complete search history.

(56) References Cited

U.S. PATENT DOCUMENTS

| 4,634,664 | A  | 1/1987  | Oestberg |
| 4,965,198 | A  | 10/1990 | Yamasaki |
| 4,968,607 | A  | 11/1990 | Dower |
| 5,034,316 | A  | 7/1991  | Weisbart |
| 5,168,062 | A  | 12/1992 | Stinski |
| 5,231,024 | A  | 7/1993  | Moeller |
| 5,585,089 | A  | 12/1996 | Queen |
| 5,654,407 | A  | 8/1997  | Boyle |
| 5,693,762 | A  | 12/1997 | Queen |
| 5,792,838 | A  | 8/1998  | Smith |
| 5,795,967 | A  | 8/1998  | Aggarwal |
| 5,932,188 | A  | 8/1999  | Snow |
| 5,959,085 | A  | 9/1999  | Garrone |
| 6,090,382 | A  | 7/2000  | Salfeld |
| 6,140,470 | A  | 10/2000 | Garen |
| 6,623,736 | B2 | 9/2003  | Tobinick |
| 7,105,183 | B2 | 9/2006  | McGrath |
| 7,718,674 | B2 | 5/2010  | Aberg |
| 8,034,337 | B2 | 10/2011 | Simard |
| 8,034,377 | B2 | 10/2011 | Brune |
| 8,242,074 | B2 | 8/2012  | Simard |
| 8,388,956 | B2 | 3/2013  | Simard |
| 8,388,969 | B2 | 3/2013  | Simard |
| 8,398,966 | B2 | 3/2013  | Wu |
| 8,546,331 | B2 | 10/2013 | Simard |
| 8,679,489 | B2 | 3/2014  | Simard |
| 8,697,689 | B2 | 4/2014  | Cid-Nunez |
| 8,784,817 | B2 | 7/2014  | Simard |
| 9,416,172 | B2 | 8/2016  | Simard |
| 9,840,558 | B2 | 12/2017 | Simard |
| 2002/0022720 | A1 | 2/2002 | Le |
| 2002/0044919 | A1 | 4/2002 | Yu |
| 2003/0004061 | A1 | 1/2003 | Kraemer |
| 2003/0023205 | A1 | 1/2003 | Botich |
| 2003/0026806 | A1 | 2/2003 | Witte |
| 2003/0040617 | A9 | 2/2003 | Rosen |
| 2003/0175832 | A1 | 9/2003 | Marton |
| 2003/0232054 | A1 | 12/2003 | Tang |
| 2004/0097712 | A1 | 5/2004 | Varnum |
| 2004/0185514 | A1 | 9/2004 | Frostegard |
| 2004/0224893 | A1 | 11/2004 | Wang |
| 2005/0005401 | A1 | 1/2005 | Bae |
| 2005/0054019 | A1 | 3/2005 | Michaud |
| 2005/0129699 | A1 | 6/2005 | Salcedo |
| 2005/0147603 | A1 | 7/2005 | Smith |
| 2005/0276807 | A1 | 12/2005 | Skurkovich |
| 2006/0127407 | A1 | 6/2006 | Chen |
| 2006/0159775 | A1 | 7/2006 | McGrath |

(Continued)

FOREIGN PATENT DOCUMENTS

| AU | 2007202323 | 6/2007 |
| CA | 2426384    | 4/2003 |

(Continued)

OTHER PUBLICATIONS

Martin-Ezquerra et al. Use of biological treatments in patients with hidradenitis suppurativa. Giornale Italiano di Dermatologia e Venereologia. Journal on Dermatology and Sexually Transmitted Diseases. vol. 152(4):373-8, Aug. 2017. Article first published online Dec. 16, 2016. (Year: 2017).*

Tzanetakou, Vassiliki, et al.: "Safety and Efficacy of Anakinra in Severe Hidradenitis Suppurative," JAMA Dermatology, 2016, vol. 152, No. 1:52-29.

Carrasco, Daniel et al.: "An Open Label, Phase 2 Study of MABp1 Monotherapy for the Treatment of Acne Vulgaris and Psychiatric Comorbidity," Journal of Drugs in Dermatology, Jun. 2015, vol. 14, Issue 6:560-564.

Kanni, Theodora, et al.: "MABp1 Targeting IL-1alpha for moderate to severe hidradenitis suppurativa not eligible for adalimumab: A randomized study," Journal of Investigative Dermatology, 2018, vol. 138:795-801.

Riis, Peter Theut et al.: "Investigational drugs in clinical trials for hidradenitis suppurativa," Expert Opinion on Investigational Drugs, 2018, vol. 27, No. 1:43-53.

(Continued)

*Primary Examiner* — Elizabeth C. Kemmerer
*Assistant Examiner* — Regina M DeBerry
(74) *Attorney, Agent, or Firm* — Ice Miller LLP

(57) ABSTRACT

Hidradenitis suppurativa can be treated by administering a pharmaceutical composition that includes a pharmaceutically acceptable carrier and a therapeutically effective amount of an agent that selectively binds IL-1α.

18 Claims, 12 Drawing Sheets

(56) References Cited

U.S. PATENT DOCUMENTS

| | | |
|---|---|---|
| 2007/0071675 A1 | 3/2007 | Wu |
| 2008/0050310 A1 | 2/2008 | Ebens, Jr. |
| 2009/0123415 A1 | 5/2009 | Simard |
| 2009/0191149 A1 | 7/2009 | Simard |
| 2009/0215992 A1 | 8/2009 | Wu |
| 2009/0258070 A1 | 10/2009 | Burnier |
| 2009/0291081 A1 | 11/2009 | Hsieh |
| 2009/0298096 A1 | 12/2009 | Simard |
| 2010/0040574 A1 | 2/2010 | Simard |
| 2010/0047239 A1 | 2/2010 | Wu |
| 2010/0068212 A1 | 3/2010 | Simard |
| 2010/0221179 A1 | 9/2010 | Hsieh |
| 2011/0008282 A1 | 1/2011 | Simard |
| 2011/0142761 A1 | 6/2011 | Wu |
| 2011/0311547 A1 | 12/2011 | Simard |
| 2012/0015384 A1 | 1/2012 | Simard |
| 2012/0045444 A1 | 2/2012 | Simard |
| 2012/0231012 A1 | 9/2012 | Simard |
| 2012/0251548 A1 | 10/2012 | Simard |
| 2012/0275996 A1 | 11/2012 | Hsieh |
| 2013/0039921 A1 | 2/2013 | Simard |
| 2013/0078258 A1 | 3/2013 | Simard |
| 2013/0195877 A1 | 8/2013 | Simard |
| 2013/0287788 A1 | 10/2013 | Simard |
| 2014/0086933 A1 | 3/2014 | Simard |
| 2015/0024031 A1 | 1/2015 | Rabinow |
| 2016/0024190 A1* | 1/2016 | Ohsawa ............ C07K 16/1271 424/165.1 |

FOREIGN PATENT DOCUMENTS

| | | |
|---|---|---|
| CN | 1431909 A | 7/2003 |
| CN | 1662557 | 8/2005 |
| CN | 101472948 | 7/2009 |
| EP | 0267611 | 5/1988 |
| EP | 0659766 | 6/1995 |
| JP | 2004285057 | 10/2004 |
| WO | 9006371 | 6/1990 |
| WO | 9524917 A1 | 9/1995 |
| WO | 9635719 | 11/1996 |
| WO | 0120828 | 3/2001 |
| WO | 0233094 | 4/2002 |
| WO | 2004100987 | 11/2004 |
| WO | 2006001967 | 1/2006 |
| WO | 2007015128 | 2/2007 |
| WO | 2007039552 | 4/2007 |
| WO | 2007120828 | 10/2007 |
| WO | 2007132338 | 11/2007 |
| WO | 2007135546 | 11/2007 |
| WO | 2009148575 A1 | 12/2009 |
| WO | 2010030979 | 3/2010 |
| WO | 2010087972 | 8/2010 |
| WO | 2011153477 | 12/2011 |
| WO | 2011159976 | 12/2011 |
| WO | 2012027324 | 3/2012 |
| WO | 2012034039 | 3/2012 |
| WO | 2012135812 | 10/2012 |
| WO | 2013043973 | 3/2013 |
| WO | 2014055541 | 4/2014 |
| WO | 2014055544 | 4/2014 |

OTHER PUBLICATIONS

International Search Report issued in corresponding international patent application No. PCT/IB2018/000209 dated Jul. 5, 2018.
Murota, H. et al., "Exacerbating factors of itch in atopic dermatitis," Allergology International, 2017, No. 66:8-13.
Fenini, G. et al., "Potential of IL-1, IL-18 and Inflammasome Inhibition for the Treatment of Inflammatory Skin Diseases," Frontiers in Pharmacology, May 2017, vol. 8: 1-20.
Kelekis, N.L. et al., "Ultrasound aids and diagnosis and severity assessment of hidradenitis suppurativa", British Journal of Dermatology, 2010, vol. 162, Issue 6, pp. 1395-1416.
Kimball, A.B., et al., "Assessing the validity, responsiveness and meaningfulness of the Hidradenitis Suppurativa Clinical Response (HiSCR) as the clinical endpoint for hidradenitis suppurativa treatment", British Journal of Dermatology, 2014, vol. 171, Issue 6, pp. 1434-1442.
Giamarellos-Bourboulis, Evangelos J., MABp1 in Hidradenitis Suppurativa Refractory to Adalimumab, ClinicalTrials.gov, Identifier: NCT02643654; Dec. 31, 2015.
Amicon Ultra2001; Millipore technical datasheet; 9 pages.
Apte, Ron N., et al., Effects of micro-environment—and malignant cell-derived interleukin-1 in carcinogenesis, tumour invasiveness and tumour-host interactions, European Journal of Cancer, 2006, vol. 42:751-759.
Barkley, D.E.H. et al: "Cells with dendritic morphology and bright interleukin-1 alpha staining circulate in the blood of patients with rheumatoid arthritis," Clin.Exp.Immmunol., 1990, vol. 80:25-31.
Beasley, Debbie and Angela L. Cooper: "Constitutive expression of interleukin-1 alpha precursor promotes human vascular smooth muscle cell proliferation," American Physiological Society, 1999, No. 276:H901-H912.
Belge, Kai-Uwe et al., The Proinflammatory CD14+ CD16+DR++ Monocytes Are a Major Source of TNF1, The Journal of Immunology, 2002, vol. 168:3536-3542.
Bendtzen, Klaus et al., Detection of Autoantibodies to Cytokines, Molecular Biotechnology, 2000, vol. 14, 14 pages.
Bendtzen, Klaus et al., High-Avidity Autoantibodies to Cytokines, Trends Immunology Today, May 1998, vol. 19, No. 5 209, 3 pages.
Bonifati, C. et al.: "IL-1alpha, IL-1beta and psoriasis: conflicting results in the literature. Opposite behaviour of the two cytokines in lesional or non-lesional extracts of whole skin," Journal of Biological Regulators and Homeostatic Agents, Oct. 1997, vol. 11, No. 4:133-136.
Boselli, Joseph et al: Fibronectin: Its relationshp to basement membranes, Light Microscopic Studies, Cell.Res., vol. 5, 1981:391-404.
Braddock, M. et al., Therapeutic potential of targeting IL-1 and IL-18 in inflammation, Expert Opin. Biol. Ther., 2004, vol. 4, No. 6:8476-860.
Buchan, G. et al: "Interleukin-1 and tumour necrosis factor mRNA expression in rheumatoid arthritis: prolonged production of IL-1alpha," Clin. Exp. Immunol. (1988), vol. 73:449-455.
Chamberlain, R.S. et al., Innovations and strategies for the development of anticancer vaccines, Exp. Opin. Pharmacother., 2000, vol. 1(4)603-614.
Chang, C.H. et al., "Interleukin-1alpha released from epithelial cells after adenovirus type 37 infection activates intercellular adhesion molecule 1 expression on human vascular endothelial cells," Journal of Virology, Jan. 2002, vol. 76, No. 1:427-431.
Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.
Clinical Trial Review: "Acne," Journal of Drugs in Dermatology (JD online Today), Jun. 2012, vol. 11, Issue 6:1-3; <<http://jddonline.com/articles/dermatology/S1545961612P0780X/1>>, last visited on Jan. 17, 2017, Abstract.
Clinical Trial Review: Acne; <<http://jddonline.eom/articles/dermatology/S1545961612P0780X/1>>, last visited on Oct. 16, 2014; 3 pages, Abstract.
Clinton Steven K. et al., Interleukin-1 gene expression in rabbit vascular tissue in vivo, American Journal of Pathology, Apr. 1991, vol. 138, No. 4:1005-1014.
Costelli, Paola et al: "Interleukin-1 receptor antagonist (IL-1ra) is unable to reverse cachexia in rats bearing an ascites hepatoma (Yoshida AH-130)," Cancer Letters 95, 1995, pp. 33-38.
Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.
Dekker, S.K. et al: "Characterization of interleukin-1alpha-induced melanoma cell motility: inhibition by type I and type II receptor-blocking monoclonal antibodies," Melanoma Research, 1997, vol. 7:223-230.

(56) References Cited

OTHER PUBLICATIONS

Dinarello, Charles A. et al: "Treating inflammation by blocking interleukin-1 in a broad spectrum of diseases," Nature Reviews/Drug Discovery, Aug. 2012, vol. 11: 633-652.
Dinarello, Charles A. et al., Anticytokine strategies in the treatment of the systemic inflammatory response syndrome, The Journal of the American Medical Association, Apr. 1993, vol. 269, No. 14:1829-1835.
Dinarello, Charles A., Biologic basis for interleukin-1 in disease, Blood, Mar. 1996, vol. 87, No. 6:2095-2147.
Dinarello, Charles A., Modalities for reducing interleukin 1 activity in disease, TiPS, May 1993 vol. 14:155-159.
Dinarello, Charles A., The role of interleukin-1 in disease, The New England Journal of Medicine, 1993, vol. 328, No. 2:106-113.
Dinarello, Charles A., Therapeutic strategies to reduce IL-1 activity in treating local and system inflammation, Current Opinion in Pharmacology, 2004, vol. 4:378-385.
El-Osta, Hazem et al.: "Successful treatment of Castleman's Disease with Interleukin-1 receptor antagonist (Anakinra)," Molecular Cancer Therapy, 2010, vol. 9:1485-1488.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
Fong Y; Moldawer L L; Marano M; Wei H; Barber A; Manogue K; Tracey K J; Kuo G; Fischman D A; Cerami A; et al., "Cachectin/TNF or IL-1 alpha induces cachexia with redistribution of body proteins.", American Journal of Physiology, American Physiological Society, US, US, (Mar. 1, 1989), vol. 256, No. 3, ISSN 0002-9513, pp. R659-R665, XP009184008.
Francois Mach., "Toward New Therapeutic Strategies Against Neointimal Formation in Restenosis", Arterioscler Thromb Vasc Biol, (2000), vol. 20, pp. 1699-1700, XP055244035.
Fujii, Masakazu et al.: "A case of advanced gastric cancer with carcinomatous ascites successfully treated with intraperitoneal administration of CDDP and TS-1," Japanese Journal of Gastoenterological Surgery, 2006, vol. 39:189-195, Eng Abs Only.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.
Garrone P et al, Generation and characterization of a human monoclonal autoantibody that acts as a high affinity interleukin-1 alpha specific inhibitor, Molecular Immunology, Pergamon, vol. 33, No. 7-8, pp. 649-658.
GenBank entry AY510107.1, *Homo sapiens* 9F11 monoclonal IgM antibody light chain mRNA, complete cds, 2005 (retrieved from the Internet on Apr. 23, 2010, <http://www.ncbi.nlm.nih.gov/nuccore/41388185>, 1 page.
Gonzalez-Lopez, M.A. et al: "New-onset psoriasis following treatment with the interleukin-1 receptor antagonist anakinra," British Journal of Dermatology, May 2008, vol. 158, No. 5:1146-1148.
Grahame, V. et al: "The Psychological Correlates of Treatment Efficacy in Acne," Dermatol Psychosom, 2002, vol. 3:119-125.
Griffiths, Andrew D. et al., Human anti-self antibodies with high specificity from phage display libraries, the EMBO Journal, 1993, vol. 12, No. 2:725-734.
Hansen, M. B. et al., Sex-and age-dependency of IgG auto-antibodies against IL-1alpha in healthy humans, European Journal of Clinical Investigation, 1994, vol. 24:212:218.
Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.
Heine, GH., et al., CD14++CD16+ monocytes but not total monocyte numbers predict cardiovascular events in dialysis patients, Kidney International, 2008, vol. 73:622-629.
Heyderman, R.S. et al: "Modulation of the endothelial procoagulant response to lipoploysaccharide and tumour necrosis factor-alpha in-vitro: The effects of dexamethasone, pentoxifylline, iloprost and a polyclonal anti-human IL-1alpha antibody, " Inflamm Res, vol. 44, 1995:275-280.
Hoge, E.A. et al: "Broad spectrum of cytokine abnormalities in panic disorder and posttraumatic stress disorder," Depression and Anxiety, vol. 26, No. 5, May 2009:447-455; Abstract only.
Hong, David S. et al: "Abstract A211: A phase I study of MABp1, a first-in-human, first-true human monoclonal antibody against the Il-1 in patients with advanced cancer," Molecular Cancer Therapeutics, 2011, (1 page).
Hong, David S. et al: "MABp1, a first-in-class true human antibody targeting interleukin-1alpha in refractory cancers: an open-label, phase 1 dose-escalation and expansion study," Lancet Oncol, 2014, vol. 15:656-66.
Horai, R. et al., Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J. Exp. Med, 1998, vol. 187, No. 9:1463-1475.
Huey-Huey Chua et al., Regulation of IAPs Gene Family by Interleukin-1a and Epstein-Barr Virus in Nasopharyngeal Carcinoma, Head & Neck 30, No. 12 (2008): 1575-85.
Ito, R. et al., Interleukin 1 alpha acts as an autocrine growth stimulator for human gastric carcinoma cells, Cancer Research, Sep. 1993, vol. 53:4102-4106.
Iwahashi, Mitsuhiro et al., Expression of Toll-Like Receptor 2 on CD16+ Blood Monocytes and Synovial Tissue Macrophages in Rheumatoid Arthritis, Arthritis and Rheumatism, 2004, vol. 50, No. 5:1457-1467.
Janik, John E. et al: "Interleukin 1alpha increases serum leptin concentrations in humans," Journal of Clinical Endocrinology and Metabolism, vol. 92, No. 9, 1997: 3084-3086.
Jefferis, Roy: "Antibody therapeutics: isotype and glycoform selection," Expert Opin. Biol. Ther., ISSN 1471-2598, (2007) 7 (9):1401-1413.
Joosten, Leo A.B. et al: "Anticytokine Treatment of Established Type II Collagen-Induced Arthritis in DBA/1 MICE," Arthritis & Rheumatism, May 1996, vol. 39, No. 5:797-809.
Joosten, M. et al: "Amelioration of established collagen-induced arthritis (CIA) with anti-IL-1," Agents Actions. vol. 41, Special Conference Issue, 1994:C174-C176.
Jouvenne, P. et al., High levels of neutralizing autoantibodies against IL-1alpha are associated with a better prognosis in chronic polyarthritis: a follow-up study, Scand. J. Immunol., 1997, vol. 46:413-418.
Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717, Abstract Only.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Kanni, T. et al., "MABpI Targeting IL-1a for Moderate to Severe Hidradenitis Suppurativa Not Eligible for Adalimumab: A Randomized Study", Journal of Investigative Dermatology, (Nov. 10, 2017), vol. 138, No. 4, ISSN 1523-1747, pp. 795-801, XP055532244.
Kasahara, T. et al., Preparation and characterization of polyclonal and monoclonal antibodies against human interleukin 1 alpha (IL 1 alpha), The Journal of Immunology, Mar. 1987, vol. 138, No. 6:1804-1812.
Kaymak, Yesim et al: "Comparison of depression, anxiety and life quality in acne vulgaris patients who were treated with either isotretinoin or topical agents, The International Society of Dermatology," 2009, vol. 48:41-46.
Kumar, Suresh, et al: "Interleukin-1alpha promotes tumor growth and cachexia in MCF-7 xenograft model of breast cancer," American Journal of Pathology, 2003, vol. 163:2531-2541.
Kurokawa, Ichiro et al: "New developments in our understanding of acne pathogenesis and treatment," Experimental Dermatology, vol. 18, 2009:821-832.

(56) References Cited

OTHER PUBLICATIONS

Larrick, James W. et al., Prospects for the therapeutic use of human monoclonal antibodies, Journal of Biological Response Modifiers, 1986, vol. 5:379-393.
Larsen C.M. et al. Interleukin-1-receptor antagonist is type 2 diabetes mellitus. New England Journal of Medicine, 2007, vol. 356, p. 1517-1526.
Larsen, C.M., et al. Sustained effects of interleukin-1 receptor antagonist treatment in type 2 diabetes. Diabetes Care, 2009, vol. 32, p. 1663-1668.
Levetan, C. Oral antidiabetic agents in type 2 diabetes. Current Medical Research and Opinion, 2007, vol. 23, No. 4, p. 945-952.
Lewis, Anne M. et al: "Interleukin-I and cancer progression: the emerging role of interleukin-1 receptor antagonist as a novel therapeutic agent in cancer treatment," Journal of Translational Medicine, 2006, vol. 4, No. 48:1-12.
Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.
Lindqvist, E. et al., Prognostic laboratory markers of joint damage in rheumatoid arthritis, Ann Rheum Dis, 2005, vol. 64:196-201.
Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.
Lundberg, Ingrid et al., "Cytokine production in muscle tissue of patients with idiopathic inflammatory myopathies," Arthritis & Rheumatism, May 1997, vol. 40, No. 5:865-874.
Ma, Joseph D. et al: "Novel investigational biologics for the treatment of cancer cachexia," Expert Opin. Biol. Ther., 2014, vol. 14(8):1113-1120.
Mach, Francois: "Toward new therapeutic strategies against neointimal formation in restenosis," Arterioscler Thromb Vasc Biol, vol. 20, 2000:1699-1700.
Madeddu, Clelia and Mantovani, Giovanni: "An update on promising agents for the treatment of cancer cachexia," Current Opinion in Supportive and Palliative Care, 2009, vol. 3:258-262.
Mandinov, L. et al.: "Inhibition of in-stent restenosis by oral copper chelation in porcine coronary arteries," Am J Physiol Heart Circ Physiol, 2006, vol. 291:H2692-H2697.
Mariotti, Massimo et al., Iterleukin 1 alpha is a marker of endothelial cellular senescent, Immunity & Ageing, Research, Apr. 2006, vol. 3, No. 4:1-6.
Marques-Deak, Andrea et al: "Measurement of cytokines in sweat patches and plasma in healthy women: Validation in a controlled study," Journal of Immunological Methods, vol. 315, 2006: 99-109.
McHale, Julie F. et al., TNF-alpha and IL-sequentially induce endothelial ICAM-1 and VCAM-1 expression in MRL/lpr lupus-prone mice, The American Association of Immunologists, 1999, vol. 163:3993-4000.
Merhi-Soussi, F. et al., Interleukin-1 plays a major role in vascular inflammation and atherosclerosis in male apolipoprotein E-knockout mice, Cardiovacular Research, 2006, vol. 66:583-593.
Miossec, P., Anti-interleukin 1alpha autoantibodies, Ann Rheum Dis, 2002, vol. 61:577-579.
Mizutani, H.: "Endogenous neutralizing anti-II-1alpha antibodies in inflammatory skin diseases: possible natural inhibitor for over expressed epidermal IL-1," 1999, Journal of Dermatological Science, vol. 20:63-71.
Niki, Y, et al. Membrane-associated IL-1 contributes to chronic synovitis and cartilage destruction in human IL-1 alpha transgenic mice. J. Immunology, 2004, vol. 172, No. 1, p. 577-584.
Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.
Ogushi, F. et al., Autoantibodies to IL-1alpha in sera from rapidly progressive idiopathic pulmonary fibrosis, The Journal of Medical Investigation, 2001, vol. 48:181-189.

Oldenburg, H.S.A., et al. Cachexia and the acute-phase protein response in inflammation are regulated by interleukin-6. Eur. J. Immunol., 1993, vol. 23, p. 1889-1894.
Oriuchi, Noboru et al: "Current status of cancer therapy with radiolabeled monoclonal antibody," Annals of Nuclear Medicine, vol. 19, No. 5, 2005:355-365.
Orjalo, Arturo V. et al.: "Cell surface-bound IL-1 alpha is an upstream regulator of the senescence-associated IL-6/ IL-8 cytokine network," PNAS, 2009, vol. 106, No. 40:17031-17036.
Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.
Pazzaglia, Laura et al: "Activation of Metalloproteinases-2 and -9 by Interleukin-1alpha in S100A4-positive Liposarcoma Cell Line: Correlation with Cell Invasiveness," Anticancer Research, 2004, vol. 24:967-972.
Rectenwald et al., "Direct Evidence for Cytokine Involvement in Neointimal Hyperplasia,"; Circulation, vol. 102, pp. 1697-1702, Oct. 3, 2000.
Rhim, JH, et al.: "Cancer cell-derived IL-1alpha induces Il-8 release in endothelial cells," J Cancer Res Clin Oncol, Jan. 2008, vol. 134(1):45-50. Epub Jul. 11, 2007; (Abstract only).
Ron N. Apte et al., The Involvement of IL-1 in Tumorigenesis, Tumor Invasiveness, Metastasis and Tumor-Host Interactions, Cancer and Metastasis Reviews 25, No. 3 (Sep. 1, 2006): 387-408.
Ross, C. et al., Increased in vivo antibody activity against interferon alpha, interleuking-1alpha, and interleukin-6 after high-dose Ig therapy, Blood, Sep. 1997, vol. 90, No. 6:2376-2380.
Ross, Christian, et al., High avidity IFN-neutralizing antibodies in pharmaceutically prepared human IgG, J. Clin. Invest., May 1995, vol. 95:1974-1978.
Rossi, Silvia et al.: "Interleukin-1 beta causes anxiety by interacting with the endocannabinoid system," The Journal of Nleuroscience, Oct. 3, 2012, vol. 32, No. 40:13896-13905.
Rubinow, David R. et al: "Reduce anxiety and depression in cystic acne patients after successful treatment with oral isotretinoin," Journal of the American Academy of Dermatology, 1987, vol. 17, No. 1:25-32.
Saitta, P. et al: "An Update on the Presence of Psychiatric Comorbidities in Acne Patients, Part 2: Depression, Anxiety, and Suicide," CUTIS, Aug. 2011, vol. 88:92-97.
Sakurai, T. et al.: "Hepatocyte Necrosis Induced by Oxidative Stress and IL-1alpha Release Mediate Carcinogen-Induced Compensatory Proliferation and Liver Tumorigenesis," Cancer Cell, Aug. 12, 2008, vol. 14:156-165.
Salfeld Jochen G, "Isotype selection in antibody engineering.", Nature Biotechnology, vol. 25, No. 12, ISSN 1546-1696, pp. 1369-1372.
Sandborg, Christy L. et al., Modulation of IL-1alpha, IL-1beta, and 25K Mr Non-IL-1 activity released by human mononuclear cells, Journal of Leukocyte Biology, 1989, vol. 46:417-427.
Satoh, H. et al., Characterization of anti-IL-1alpha autoantibodies in the sera from healthy humans, Immunopharmacology, 1994, vol. 27:107-118.
Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.
Sawai, H. et al: "Interleukin-1 alpha enhances the aggressive behavior of pancreatic cancer cells by regulating the alpha 6 beta I-integrin and urokinase plasminogen activator receptor expression," MC Cell Biology, 2006:1-13.
Schlitt, Axel et al., CD14+D16+ monocytes in coronary artery disease and their relationship to serum TNF-alpha levels, Thromb Haemost, 2004, vol. 92:419-424.
Shirakawa, F. et al., Autocrine stimulation of interleukin 1 alpha in the growth of adult human T-cell leukemia cells, Cancer Research, Mar. 1989, vol. 49:1143-1147.
Shreeniwas, R. et al: "Hypoxia-mediated induction of endothelial cell interleukin-1alpha: an autocrine mechanism promoting expres-

(56) References Cited

OTHER PUBLICATIONS sion of leukocyte adhesion molecules on the vessel surface," 1992, J. Clin. Invest., vol. 90:2333-2339.
Simard, John: "Early Results from XBiotech's Clinical Study in Cachexia Hint at Breakthrough Treatment," XBiotech News: Clinical Study in Cachex . . . , 2011, (3 pages), (retrieved from the Internet <http://www.xbiotech.com/about/news/early-results-from-xBiotechs-clinical-study-in-cachexia.html>, last visited on Jul. 22, 2015.
Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.
Sturlan, Sanda, et al: "In vivo gene transfer of murine interleukin-4 inhibits colon-26-mediated cancer cachexia in mice," Anticancer Research, 2002, vol. 22:2547-2554.
Sunahara, N. et al., Differential determination of recombinant hum interleukin-1 alpha and its deamidated derivative by two sandwich enzyme immunoassays using monoclonal antibodies. Comparison with a polyclonal antibody-based competitive enzyme immunoassay., J Immunol Methods, 1989, vol. 119:75-82 (Abstract only).
Suzuki, Hiroshi et al., Demonstration of Neutralizing Autoantibodies against Il-1alpha in sera from patients with rheumatoid arthritis, The Journal of Immunology, Oct. 1, 1990, vol. 145, No. 7:2140-2146.
Svenson M, et al. Cytokine vaccination: neutralising IL-1alpha autoantibodies induced by immunisiation with homologous IL-1alpha. Journal of Immunological Methods, 2000, vol. 236, No. 1-2, p. 1-8.
Svenson, M. et al., Antibody to granulocyte-macrophage colony-stimulating factor is a dominant anti-cytokine activity in human IgG preparations, Blood, Mar. 1998, vol. 91, No. 6:2054-2061.
Svenson, M. et al., Binding of Cytokines to Pharmaceutically Prepared Human Immunoglobulin, J. Clin. Invest., Nov. 1993, vol. 92:2533-2539.
Svenson, M. et al., Distribution and characterization of autoantibodies to interleukin 1 alpha in normal human sera, Scand. J. Immunol., 1990, vol. 32:695-701.
Svenson, M. et al., Effects of human anti-IL-1alpha autoantibodies on receptor binding and biological activities of IL-1 alpha, Cytokine, Mar. 1992, vol. 4, No. 2:125-133.
Svenson, M. et al., IgG Autoantibodies against Interleuking 1 alpha in sera of normal individuals, Scand. J. Immunol., 1989, vol. 29:489-492.
Szabo, K. et al: "Interleukin-1A +4845(G>T) polymorphism is a factor predisposing to acne vulgaris," Tissue Antigens, 2010, vol. 76:411-415.
Tamura, Sumie et al: "Involvement of human interleukin 6 in experimental cachexia induced by a human uterine cervical carcinoma xenograft," Clinical Cancer Research, Nov. 1995, vol. 1:1353-1358.
Tsunoda, Yasuaki et al., "Immunohistochemical study of cytokines and extracellular matrices at invasive sites of human colon cancers," Biotherapy, May 1996, vol. 10, No. 5:789-790; Abstract only.
U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011, 3 pages.
U.S. Appl. No. 13/162,705, (Simard) filed Jun. 17, 2011, "Arthritis Treatment," not yet published; 18 pages.
U.S. Appl. No. 13/215,464, (Simard) filed Aug. 23, 2011, "Treatment for Neoplastic Diseases," not yet published; 17 pages.
U.S. Appl. No. 13/224,913, (Simard) filed Sep. 2, 2011, "Interleukin-1 Alpha Antibodies and Methods of Use," not yet published; 25 pages.
U.S. Appl. No. 13/224,975, (Simard) filed Sep. 2, 2011, "Interleukin-1 Alpha Antibodies and Methods of Use," not yet published; 25 pages.
U.S. Appl. No. 13/225,004, (Simard) filed Sep. 2, 2011, "Interleukin-1 Alpha Antibodies and Methods of Use," not yet published; 25 pages.
U.S. Appl. No. 13/225,029, (Simard) filed Sep. 2, 2011, "Interleukin-1 Alpha Antibodies and Methods of Use," not yet published; 25 pages.
Uefuji, K. et al: "Increased expression of interleukin-1alpha and cyclooxygenase-2 in human gastric cancer: a possible role in tumor progression," 2005, Anticancer Research, vol. 25:3225-3230.
Ulrich, C. et al., Proinflammatory CD14+CD16+ Monocytes are Associated with Subclinical Atherosclerosis in Renal Transplant Patients, American Journal of Transplantation, 2008, vol. 8:103-110.
Van Asseldonk, E.J.P., et al. One week treatment with the IL-1 receptor antagonist anakinra leads to a sustained improvement in insulin sensitivity in insulin resistant patients with type 1 diabetes mellitus. Clinical Immunology, 2015, vol. 160, p. 155-162.
Vazquez A et al, "Interleukin 1 can replace monocytes for the specific human B-cell response to a particulate antigen", Cellular Immunology, Academic Press, San Diego, CA, US, vol. 86, No. 2, pp. 287-298.
Von Der Thusen, Jan H., et al., Interleukins in atherosclerosis: Molecular pathways and therapeutic potential, Pharmacol Rev, 2003, vol. 55, No. 1:133-166.
Voronov, E. et al: "IL-1 is required for tumor invasiveness and angiogenesis," PNAS, 2003, vol. 100, No. 5:2645-2650.
Wake, R. et al., Gender differences in ischemic heart disease, Recent Patents on Cardiovascular Drug Discovery, 2009, vol. 4:234-240.
Wood D D et al, "Release of Interleukin-1 From Human Synovial Tissue In-Vitro", Arthritis and Rheumatism, vol. 28, No. 8, pp. 853-862.
Xbiotch IND for the treatment of Chronic Myelogenous Leukemia, pp. 1 (Year: 2010).
XBiotech, Inc. Pressrelease: "XBiotech Files Investigational New Drug (IND) Application with the FDA for the treatment of Chronic Myelogenous Leukemia," Evaluate, Nov. 22, 2010, 2 pages.
Yamada, Takayuki et al.: "Growth Dependency of a new human pancreatic cancer cell line, YAPC, on autocrine interleukin-1 alpha stimulation," Int. J. Cancer, 1998, vol. 76:141-147.
Yanni, G. et al: "Intramuscular gold decreases cytokine expression and macrophage numbers in the rheumatoid synovial membrane," Annals of the Rheumatic Diseases, 1994, vol. 53:315-322.
Yoichi Matsuo et al., IL-1a Secreted by Colon Cancer Cells Enhances Angiogenesis: The Relationship between IL-1a Release and Tumor Dells' Potential for Liver Metastasis, Journal of Surgical Oncology 99, No. 6 (2009): 361-367.
Yost, J. and J.E. Gudjonsson: "The role of TNF inhibitors in psoriasis therapy: new implications for associated comorbidities," Medicine Reports, May 2009, vol. 1, No. 30:1-4.
Zhu, Y. et al., "The clinical study about interleukin-1 and tumor necrosis factor alpha in hepatocirrhosis," Chinese Journal of Clinical Hepatology, 2001, vol. 17, Issue 4: 233-234.
Ziegler-Heitbrock, Loems, The CD14+CD16+ blood monocytes: their role in infection and inflammation, Journal of Leukocyte Biology, Mar. 2007, vol. 81:584-592.
Campbell et al., "Totipotency or multipotentiality of cultured cells: Applications and Progress", Theriology, 1997, vol. 47, No. 1, pp. 63-72.
Chamberlain, Janet et al., "Interleukin-1B and signaling of Interleukin-1 in Vascular Wall and Circulating Cells Modulates the Extend of Neointima Formation in Mice," American Journal of Pathology, vol. 168, No. 4, pp. 1396-1403, Apr. 2006.
Clinical trial: NCT02643654, "MABp1 in Hidradenitis Suppurativa Refractory to Adalimumab", Oct. 9, 2016 (Oct. 9, 2016), Retrieved from the Internet: URL: https://clinicaltrials .gov /ct2/h istory /NCT02643654 ?V 3= View#StudyPageTop, 10 pages.
Feldman et al., "Diagnosis and Treatment of Acne", American Family Physician, 69(9):2123-30, 2004.
Hessam, et al., "Microbial Profile and Antimicrobial Susceptibility of Bacteria Found in Inflammatory Hidradenitis Suppurativa Lesions," Skin Pharmacol Physiol 2016;29:161-167.
Janeway, C.A., Jr. et al, "The induction, measurement, and manipulation of the immune response" in ImmunoBiology, The Immune System in Health and Disease, Third Edition (Garland Publishing Inc., New York and London, 1997), 9 pages.
Kaji, Mitsuhito et al, "E-selection expression induced by pancreas-carcinoma-derived interleukin-1alpha results in enhanced adhesion of pancreas-carcinoma cells to endothelial cells", Intl Journal of Cancer, vol. 60, Issue 5, pp. 712-717, Mar. 3, 1995 (abstract).

(56) References Cited

OTHER PUBLICATIONS

Kamari et al., "Reduced atherosclerosis and inflammatory cytokines in apolipoprotein-E-deficient mice lacking bone marrow-derived interleukin-1a," Biochemical and Biophysical Research Communications, vol. 405, pp. 197-203 (2011).
Kaufman et al., "Transgenic Analysis of a 100-kb Human B-Globin Cluster-Containing DNA Fragment Propagated as a Bacterial Artificial Chromosome", Blood, 1999, vol. 94, pp. 3178-3184.
Kishore et al., "C1q: structure, fuction, and receptors", Immunopharmacology, 2000, vol. 49, pp. 159-170.
Kurzrock et al., "Interleukin-1 receptor antagonist levels predict favorable outcome after bermekimab, a first-in-class true human interleukin-1a antibody, in a phase III randomized study of advanced colorectal cancer", Oncolmmunology Journal, 2019, vol. 8, No. 3, pp. 1-7.
Lapins et al., "Coagulase-negative staphylococci are the most common bacteria found in cultures from the deep portions of hidradenitis suppurativa lesions, as obtained by carbon dioxide laser surgery". British Journal of Dermatology 1999; 140: 90-95.
Larionov et al., "Expression of a2-macroglobulin, neutrophil elastase, and interleukin-1a differs in early-stage and late-stage atherosclerotic lesions in the arteries of the circle of Willis," Acta Neuropathol, vol. 113, pp. 33-43, 2007.
Li, X. et al: "Interleukin-1alpha up-regulation in vivo by a potent carcinogen 7, 12-Dimethylbenz(a)anthracene (DMB) and control of DMBA-induced inflammatory responses," Cancer Research, 2002, vol. 62, pp. 417-423.
Morton, Allison C., et al., "The effect of interleukin-1 receptor antagonist therapy on markers of inflammation in non-ST elevation acute coronary syndromes: the MRC-ILA Heart Study," European Heart Journal, vol. 36, pp. 377-384 (2015).
Morton, Allison, C. et al: "Interleukin-1 receptor antagonist alters the response to vessel wall injury in a porcine coronary artery model," Cardiovascular Research, vol. 68, 2005: 493-501.
Moyer et al., "Synthesis of IL-1 Alpha and IL-1 Beta by Arterial Cells in Atherosclerosis," American Journal of Pathology, vol. 138, No. 4, pp. 951-960, Apr. 1991.
NCT01270945—Safety and Preliminary Efficacy Study of an Anti inflammatory Therapeutic Antibody in Reducing Restenosis (version 6; submitted May 15, 2012), 8 pages.
Patti et al., "Prognostic Value of Interleukin-1 Receptor Antagonist in Patients Undergoing Percutaneous Coronary Intervention," American Journal of Cardiology, vol. 89, pp. 372-376, Feb. 15, 2002.
Peigang et al., "Theory and Practice of Neurosurgical Diseases", Tianjin Science and Technology Press, 1st edition—Complications and Countermeasures of Stent Implantation, p. 123, publication date: Oct. 2011. Chinese-language publication. English translation of relevant excerpt attached. 1 page.
Schultz, et al., "Endogenous interleukin-1a promotes a proliferative and proinflammatory phenotype in human vascular smooth muscle cells," Am J Physiol Heart Circ Physiol, Jun. 2007:292(6):H2927-34.
Stark et al., "Anxiety in cancer patients", British Journal of Cancer, 83(10):1261-1267, 2000.
Sun Qinguo et al., "Coronary Heart Disease", chiefly edited by China Medical Science and Technology Press, 1st edition, "Interventional Therapy of Coronary Heart Disease", pp. 203-208, publication date: Jan. 2010. Chinese-language publication. English translation of relevant excerpt attached.
Waehre et al., "Increased Expression of Interleukin-1 in Coronsary Artery Disease With Downregulatory Effects of HMG-CoA Reducatse Inhibitors," Circulation, Apr. 27, 2004, pp. 1966-1972 (downloaded from circ.ahajournals.org on Jan. 15, 2008).
Wang et al., "Rapid analysis of gene expression (RAGE) facilitates universal expression profiling", Nuc. Acids Res. 1999, vol. 27, pp. 4609-4618.
Wei et al, "Clinical key techniques of routine operation in cardiac diagnosis and treatment", Science and Technology Literature Press, 1st edition—"Restenosis and related factors", p. 239, publication date: May 2009. Chinese-language publication. English translation of relevant excerpt attached.
Wigley et al., "Site-specific Transgene Insertion: an Approach", Reprod Fert Dev, 1994, vol. 6, pp. 585-588.
Zaragoza et al.: "Animal Models of Cardiovascular Diseases," Journal of Biomedicine and Biotechnology, vol. 2011, Article ID 497841, pp. 1-13. (2011).
Janik et al., "Phase II trial of interleukin 1 alpha and indomethacin in treatment of metastatic melanoma.", Journal of the National Cancer Institute Jan. 3, 1996 (Jan. 3, 1996), vol. 88, No. 1, pp. 44-49; https://doi.org/10.1093/jnci/88.1.44.
Mennin et al., "Screening for social anxiety disorder in the clinical settin: using the Liebowitz Social Anxiety Scale," Anxiety Disorders, 16:661-673, 2002.
Ofran et al., "Automated Identification of Complementarity Determining Regions (CDRs) Peculiar Characteristics of CDRs and B Cell Epitopes", J. Immunology 2008 181: 6230-6235.
Radke et al., "Outcome after treatment of coronary in-stent restenosis results from a systematic review using meta-analysis techniques", European Heart Journal, vol. 24, No. 3, Feb. 1, 2003 (Feb. 1, 2003), pp. 266-273, XP055265672, GB ISSN: 0195-668X, DOI: 10.1016/S0195-668X(02)00202-6.
Ramli et al., "Acne analysis, grading and computational assessment methods: an overview," Skin Research and Technology 2012; 18: 1-14.
Rishi et al., "Hospital anxiety and depression scale assessment of 100 patients before and after using low vision care: A prospective study in a teriary eye-care setting," Indian J Ophthalmol. Nov. 2017; 65(11): 1203-1208.
Snaith, R.P. The Hospital Anxiety and Depression Scale. Health Qual Life Outcomes 1, 29 (2003). (4 pages).
US National Institutes of Health, "Anakinra With or Without Dexamethasone in Treating Patients with Smoldering or Indolent Multiple Myeloma", ClinicalTrials.gov, US, (Mar. 12, 2008), pp. 1-4, ClinicalTrials.gov, URL: http://clinicaltrials.gov/c12/show/NCT00635154.
Westhuis et al., "Develepment and Validation of the Clinical Anxiety Scale: A Rapid Assessment Instrument for Empirical Practice," Educational and Psychological Measurement, 49:153-163, 1989.
Phase II trial of cetuximab in patients with previously treated non-small-cell lung cancer Hanna et al. (2006) J. Clin. Oncol. 24: 5253-5258.
Haller, M. "Converting Intravenous Dosing to Subcutaneous Dosing with Recombinant Human Hyaluronidase", Pharmaceutical Technology, Oct. 2, 2007, vol. 31, Issue 10 (Year: 2007).
Schmidt, R. "Dose-Finding Studies in Clinical Drug Development"; EurJ Clin Pharmacol (1988) 34:15-19. (Year: 1988).
Walpole et al. "The weight of nations: an estimation of adult human biomass"; BMC Public Health 2012, 12:439. (Year: 2012).
Morton, A.C. , et al., "Investigation of IL-1 Inhibition in Patients Presenting with Non-St Elevation Myocardial Infarction Acute Coronary Syndromes (The MRC ILA Heart Study), "Heart, vol. 97, Suppl 1., Jun. 2011.

\* cited by examiner

TREATMENT OF HIDRADENITIS SUPPURATIVA

CROSS-REFERENCE TO RELATED APPLICATIONS

The present application is a continuation of international patent application number PCT/IB2018/000209 filed on Feb. 16, 2018, which claims the priority of U.S. provisional patent application Ser. No. 62/459,841, entitled "Treatment of Hidradenitis Suppurativa," filed on Feb. 16, 2017.

STATEMENT AS TO FEDERALLY SPONSORED RESEARCH

Not applicable.

FIELD OF THE INVENTION

The invention relates generally to the fields of medicine, dermatology, and immunology. More particularly, the invention relates to the use of antibodies (Abs) which specifically bind interleukin-1α (IL-1α) to treat hidradenitis suppurativa.

BACKGROUND

Hidradenitis suppurativa (HS) is a chronic debilitating skin disease where nodules appearing in areas rich in apocrine glands progressively swell until they rupture and release pus through the skin. Sinus tract formation and scars result. HS is typically treated with antibiotics and surgery, but frequent relapse drastically impairs the patient's quality of life.

SUMMARY

Disclosed herein is the discovery that an agent that specifically targets IL-1α is useful for treating HS.

Accordingly, described herein are methods of reducing the severity of HS symptoms in a human subject. These methods can include the step of administering to the subject a pharmaceutical composition including a pharmaceutically acceptable carrier and an amount of an agent that selectively binds IL-1α effective to reduce the number and/or size of inflammatory lesions (e.g., nodule, abscesses, or draining fistulas), prevent their progression, reduce the pain caused by the lesions, or increase the time until new exacerbations. The agent can be an anti-IL-1α antibody (Ab) such as a monoclonal antibody (mAb) (e.g., of the IgG1 isotype), a mAb that includes a complementarity determining region (CDR) of MABp1, or MABp1.

Another aspect of the invention features a method of reducing the symptoms of HS in a human subject by administering to the subject a pharmaceutical composition including a pharmaceutically acceptable carrier and an amount of an anti-IL-1α Ab (or other agent that specifically and/or selectively binds IL-1α) effective to reduce the number and/or size of inflammatory lesions (e.g., nodule, abscesses, or draining fistulas) in the subject by at least about 10% (e.g., at least 8, 9, 10, 15, 17, 20, 30, 40, 50, 60, 70, 80, 90, or 100%) as measured by any standard dermatological test.

The anti-IL-1α Ab can be a mAb such as an IgG1. The anti-IL-1α Ab can be the mAb designated as MABp1 or a mAb that includes one or more (CDRs) of MABp1. The pharmaceutical composition can be administered to the subject by injection, infusion, subcutaneously, intravenously, intramuscularly, or intradermally. In the methods described herein, the dose can be at least 0.25 (e.g., at least 0.2, 0.5, 0.75, 1, 2, 3, 4, or 5) mg/kg, and preferably at between 1-20 mg/kg (e.g., 1, 2, 3, 4, 5, 6, 7, 8, 9, 10, 11, 12, 13, 14, 15, 16, 17, 18, 19, or 20+/−0.1, 0.2, 0.3, 0.4, 0.5, 0.6, 0.7, 0.8, or 0.9 mg/kg).

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27th Edition, Lippincott, Williams & Wilkins, 2000.

As used herein, an "antibody" or "Ab" is an immunoglobulin (Ig), a solution of identical or heterogeneous Igs, or a mixture of Igs. An "Ab" can also refer to fragments and engineered versions of Igs such as Fab, Fab', and F(ab')$_2$ fragments; and scFv's, heteroconjugate Abs, and similar artificial molecules that employ Ig-derived CDRs to impart antigen specificity. A "monoclonal antibody" or "mAb" is an Ab expressed by one clonal B cell line or a population of Ab molecules that contains only one species of an antigen binding site capable of immunoreacting with a particular epitope of a particular antigen. A "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule. An Ab that "selectively binds" a first molecule specifically binds the first molecule at a first epitope but does not specifically bind other molecules that do not have the first epitope. For example, an Ab which selectively binds IL-1alpha specifically binds an epitope on IL-1 alpha but does not specifically bind IL-1beta (which does not have the epitope).

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All patents, patent applications, and publications mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
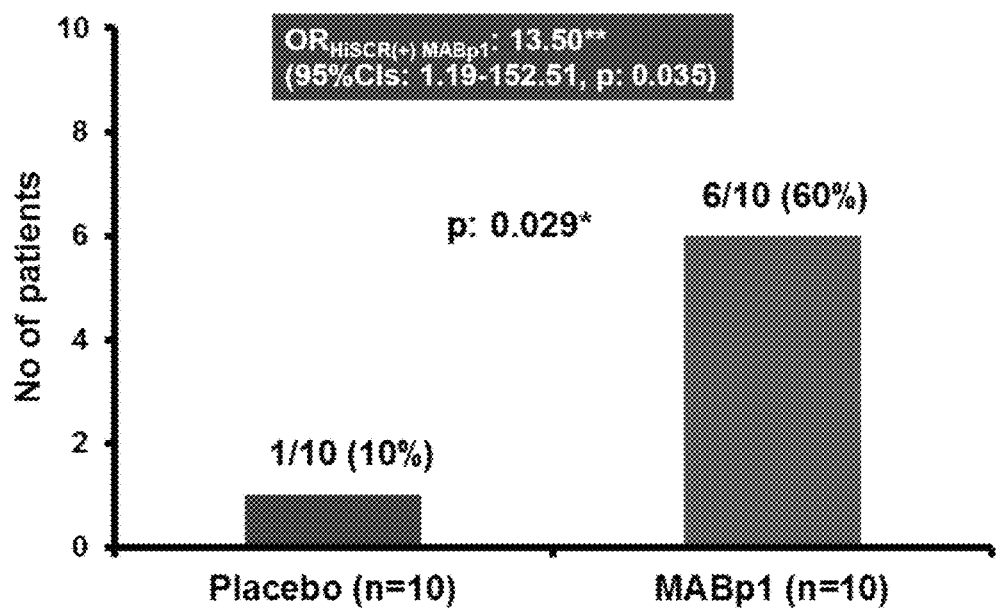
FIG. 1 is a graph showing that 60% of patients allocated to treatment with MABp1 achieved positive HiSCR at week 12 compared to 10% of the placebo group; and that the odds ratio (OR) for positive HiSCR under MABp1 was 13.50 (95% confidence intervals: 1.19-152.51; p=0.035).

The invention encompasses compositions and methods for reducing skin inflammation in HS including ameliorating one or more symptoms of a dermatological pathology in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, $49^{th}$ Edition, McGraw-Hill Medical, 2010; and Fauci et al., Harrison's Principles of Internal Medicine, $17^{th}$ Edition, McGraw-Hill Professional, 2008. Methods in dermatology are described in James et al., Andrews' Diseases of the Skin: Clinical Dermatology—Expert Consult, $11^{th}$ Ed., Saunders, 2011; and Burns et al., Rook's Textbook of Dermatology, $8^{th}$ Ed., Wiley-Blackwell, 2010.

Treatment

The compositions and methods described herein are useful for HS in a mammalian subject by administering to the subject a pharmaceutical composition including an amount of an anti-IL-1α Ab effective to improve at least one characteristic of the condition in the subject (e.g., reduce the number and/or size of nodules, abscesses, or draining fistulas or prevent their progression). The mammalian subject might be any that suffers from HS including human beings. Human subjects might be male, female, adults, children, seniors (65 and older), and those with other diseases. Particularly preferred subjects are (i) those whose disease has progressed or failed to respond after treatment with other anti-inflammatory (e.g., TNFα inhibitors) or anti-microbial agents; (ii) those with a familial history of HS; (iii) those in which other anti-inflammatory (e.g., TNFα inhibitors) or anti-microbial agents are not suitable; and (iv) those with higher than 100, 200, 300, 400, 500, or 1000 pg/ml of IL-1α in pus taken from their lesions. Subjects who have developed a human anti-human antibody response due to prior administration of therapeutic antibodies are preferred when the anti-IL-1α Ab is a true human Ab (e.g., one that is naturally expressed in a human subject) such as MABp1.

Antibodies and Other Agents that Target IL-1α

Any suitable type of Ab that specifically binds IL-1α and reduces a characteristic of HS in a subject might be used. For example, the anti-IL-1α Ab used might be mAb, a polyclonal Ab, a mixture of mAbs, or an Ab fragment or engineered Ab-like molecule such as an scFv. The Ka of the Ab is preferably at least $1 \times 10^9$ $M^{-1}$ or greater (e.g., greater than $9 \times 10^{10}$ $M^{-1}$, $8 \times 10^{10}$ $M^{-1}$, $7 \times 10^{10}$ $M^{-1}$, $6 \times 10^{10}$ $M^{-1}$, $5 \times 10^{10}$ $M^{-1}$, $4 \times 10^{10}$ $M^{-1}$, $3 \times 10^{10}$ $M^{-1}$, $2 \times 10^{10}$ $M^{-1}$, or $1 \times 10^{10}$ $M^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. Pat. No. 8,034,337B2 issued on Oct. 11, 2011. Other useful mAbs are those that include at least one but preferably all the CDRs of MABp1. CDRs may be determined according to known methods such as described in Ofran et al., J. Immunol., 181:6230, 2008; and Antibody Engineering Volume 2, 2d edition, Konterman and Dubel (eds), Springer, 2010. Abs that specifically binds IL-1α and methods of their manufacture are described in more detail in, e.g., U.S. Pat. No. 9,545,411.

While the IL-1α specific Abs described above are preferred for use in the methods described herein, in some cases, other agents that specifically target IL-1α might be used so long as their administration leads to improvement of a characteristic of HS. These other agents might include vaccines that cause the production of anti-IL-1α Abs, proteins or peptides that bind IL-1α, and small organic molecules which specifically target IL-1α. Those that do not specifically bind IL-1β are preferred because the use of such agents have been reported to worsen the symptoms of HS (e.g., Tekin et al., Indian J Dermatol Venereol Leprol 2017; 83:615-7), and others have reported that IL-1β promotes healing and repair (e.g., Bersudsky et al., Gut. 2014 April; 63(4):598-609).

Pharmaceutical Compositions and Methods

The anti-IL-1α Ab compositions (and other agents that specifically target IL-1α) may be administered in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent.

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., the skin) by, for example, topical application. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in patients as measured by the improvement in one or more symptoms of skin inflammation. As is well known in the medical arts, dosage for any one animal or human depends on many factors, including the subject's size, body surface area, age, the particular composition to be administered, sex, time and route of administration, general health, and other drugs being administered concurrently. Preferred doses range from between 1-20 mg/kg body weight (e.g., 1, 2, 3, 4, 5, 6, 7, 8, 9, 10, 11, 12, 13, 14, 15, 16, 17, 18, 19, or 20+/−0.1, 0.2, 0.3, 0.4, 0.5, 0.6, 0.7, 0.8, or 0.9 mg/kg body weight). In some cases, a single dose is effective at resolving an episode of skin inflammation. In other cases, doses may be given repeatedly, e.g., semi-weekly, weekly, bi-weekly, tri-weekly, semi-monthly, once every three weeks, monthly, bi-monthly, or as needed (if lesions recur).

Combination Treatment

HS patients treated with an agent that selectively binds IL-1☐ can also be administered other agents. For example, such patients can be treated with corticosteroids, retinoids, resorcinol, hormones, and biologics such as adalimumab or infliximab. Antimicrobials might also be used. In particular, antibiotics or other agents that target S. aureus can be used in those patients having or suspected of having S. aureus colonization or infection in one or more HS lesions. The use of antibodies that opsonize S. aureus are believed to be particularly useful. Preferred anti-S. aureus for this use are those having Fab region paratopes that specifically bind to S. aureus protein A (SpA) and Fc regions that do not bind SpA such that there are capable of mediating opsinization of S. aureus bacteria despite S. aureus's expression of antibody-neutralizing SpA. These are described in U.S. Pat. No. 9,416,172 (e.g., the antibody designated PA8-G3 therein).

EXAMPLES

Example 1—A double-blind, randomized, placebo-controlled clinical trial of the safety and efficacy of MABp1, a True Human™ antibody targeting interleukin-1α in patients with HS.

HS patients were screened from those who are currently under follow-up. Inclusion criteria were: written informed consent provided by the patient; age 18 years or older; diagnosis of HS; HS of Hurley II or III stage disease or rapidly progressive HS of Hurley I stage; presence of 3 or more inflamed nodules consistent with HS in the body; at least one of the following: a) previous failure of treatment with any anti-TNFα, regimen; b) previous relapse under treatment with any anti-TNFα, regimen; or c) unwillingness to receive subcutaneous adalimumab treatment.

Exclusion criteria were: history of systemic lupus erythematosus, of rheumatoid arthritis or of seronegative inflammatory arthritis; treatment with any biologicals or investigational agents within the last 4 weeks (or 5 half-lives, whichever is longer); history of severe allergic or anaphylactic reactions to human, humanized, chimeric, or murine monoclonal antibodies; administration of any live (attenuated) vaccine over the last 4 weeks; history of recurrent vein thrombosis or embolism compatible with anti-cardiolipin syndrome; any present serious bacterial infection namely pneumonia, endocarditis, acute pyelonephritis and intraabdominal infection; hepatic dysfunction defined as any value of transaminases, of γ-glutamyl transpeptidase or of bilirubin>2×upper normal limit; history of hematological or solid tumor malignancy, arterial hypertension, liver cirrhosis, HIV infection, and hepatitis virus B or C infection; history of episodes mimicking demyelinating disorders or a definite diagnosis of multiple sclerosis; any creatinine value above 1.5 mg/dl; intake of corticosteroids defined as daily intake of prednisone or equivalent more than 1 mg/kg for the last three weeks; neutropenia defined as <1000 neutrophils/mm3; pregnancy or lactation; history of tuberculosis (latent or active); major surgery within 28 days prior to Day 0.

Diagnosis of HS was based on the following criteria, set by the 2nd Conference of the HS foundation in San Francisco: disease onset after puberty; involvement of at least two areas of the skin rich in apocrine glands; and history of recurrent painful boils without/with drainage of pus from the affected areas. Once a patient was considered eligible for the study the following procedures were performed: thorough study of record-history and medications; thorough physical examination; skin tuberculin test (any diameter below 5 mm is considered negative); chest X-ray; serology for human immunodeficiency virus (HIV), for hepatitis B virus (HBV) and for hepatitis C virus (HCV); serum creatinine; and liver biochemistry. Only patients within normal were enrolled in the study. Patients were randomly 1:1 assigned to receive either placebo or MABp1 (XBiotech USA, Inc.) intravenously. The randomization sequence was built by an independent biostatistician. The investigational drug or matched placebo was administered intravenously with a one-hour infusion every 14 days (+/−1 day) for 12 weeks, i.e., at week 0 (baseline), week 2, week 4, week 6, week 8, week 10 and week 12 for a maximum of seven infusions. The dose of MABp1 was 7.5 mg/kg.

XILONIX™, is a sterile injectable liquid formulation of 50 mg/mL MABp1 in a stabilizing isotonic buffer (pH 6.4). Each 10-mL serum vial contains 6 ml of the formulation, and is sealed with a 20-mm grey bromobutyl stopper and flip-off aluminum seal. Product was stored at 2-8° C., with excursions to room temperature permitted. The exact composition of the drug product is shown below:

Composition of the Final Drug Product

| Ingredient | Grade | Manufacturer | Concentration |
|---|---|---|---|
| MABp1 antibody | GMP | XBiotech | 50 mg/ml |
| sodium phosphate dibasic | compendial | J T Baker | 12 mg/ml |
| citric acid monohydrate | compendial | J T Baker | 2 mg/ml |
| Trehalose•2H$_2$O (high-purity low endotoxin) | compendial | Ferro-Pfanstiehl | 60 mg/ml |
| polysorbate 80 | compendial | J T Baker | 0.2 mg/ml |
| Phosphoric acid, to adjust pH | compendial | J T Baker | 0.04 mg/ml |
| water for injection | compendial | Microbix | — |

The placebo product was manufactured following the same procedures and batch records used to manufacture the MABp1 drug product. The placebo dosage form is a sterile isotonic formulation buffer at pH 6.2-6.5. Each 10-ml Type I borosilicate glass serum vial contains 6 mL of the formulation buffer, and is sealed with a 20-mm Daikyo Flurotec butyl rubber stopper and flip-off aluminum seal. The product was stored upright at 2-8° C., with excursions to room temperature permitted. The exact composition of the Placebo Product is shown in the table below:

Composition of Placebo Product

| Ingredient | Grade | Manufacturer | Concentration |
|---|---|---|---|
| trehalose dihydrate | compendial | Ferro-Pfanstiehl (USA) | 60 mg/ml |
| sodium phosphate dibasic | compendial | J T Baker (USA) | 12 mg/ml |
| citric acid monohydrate | compendial | J T Baker (USA) | 2 mg/ml |
| Polysorbate 80 | compendial | J T Baker (USA) | 0.2 mg/ml |
| Phosphoric acid, to adjust pH | compendial | J T Baker | 0.04 mg/ml |
| water for injection | compendial | Irvine Scientific (USA) | q.s. |

XILONIX™ was diluted in a 100-mL bag of normal saline prior to infusion. The following calculations were used to determine the volume of drug product to be diluted for each study subject:

50 mg/ml drug products, 7.5 mg/kg dose:

Volume of drug product to be diluted =

$$Vd = \frac{(\text{Body Weight} \times \text{Dosage})}{50 \text{ mg/mL}}$$

(Body Weight was rounded to the nearest whole number)

Example for 70 kg Subject at 7.5 mg/kg: $Vd = \frac{(70 \text{ kg} \times 7.5 \text{ mg/kg})}{50 \text{ mg/mL}}$ $Vd = 10.5$ mL (round to one decimal place)

The calculated volume (Vd) was withdrawn from the subject's assigned vial(s) using a suitable syringe. The same amount of saline as the calculated drug was removed from the 100-ml bag. The calculated volume was then injected into the 100-mL IV bag of normal saline (0.9% NaCl), resulting in a final total volume of 100 ml. The drug product was then mixed by gently inverting the bag ten times. After priming the infusion set lines, the delivery pump was programmed to deliver 100 mL of the diluted drug product over a 1-hour period (60+/−15 minutes), with the subject being monitored for signs of an infusion reaction. Patients' visits occurred at week 0, at week 2, at week 4, at week 6, at week 8, at week 10, at week 12, at week 16, at week 20 and at week 24. At every visit the following procedures were performed.

| | Visits | | | | | | | | | |
|---|---|---|---|---|---|---|---|---|---|---|
| | 1 | 2 | 3 | 4 | 5 | 6 | 7 | 8 | 9 | 10 |
| | | | | | Weeks | | | | | |
| | 0 | 2 | 4 | 6 | 8 | 10 | 12 | 16 | 20 | 24 |
| DQLI | x | – | – | – | – | x | – | – | x | |
| Physical examination | x | x | x | x | x | x | x | x | x | x |
| HiSCR | x | x | x | x | x | x | x | x | x | x |
| PGA | x | x | x | x | x | x | x | x | x | x |
| Disease activity | x | x | x | x | x | x | x | x | x | x |
| Modified Sartorius | x | x | x | x | x | x | x | x | x | x |
| VAS for disease | x | x | x | x | x | x | x | x | x | x |
| VAS for pain | x | x | x | x | x | x | x | x | x | x |
| Photo | x | – | – | – | – | – | x | – | – | x |
| Blood sampling | x | – | – | – | –– | – | x | – | – | x |

DQLI: Dermatology Quality of Life Index
HiSCR: Hidradenitis Suppurativa Clinical Response score
PGA: Physicians' Global Assessment
VAS: Visual Analogue Scale Patients were asked to provide an assessment of the severity of their disease using the visual analogue scale (VAS) in mm They were told that 0 represents no disease activity and 100 the worst disease activity they ever felt. Patients were asked to provide one score for their overall impression about their disease and another score about the physical pain they feel. The investigators asked the patient to provide the frequency of the exacerbation of his disease and the pain felt at the affected sites. Patients were given the below DLQI score and they were asked to fill it out only at week 0, at week 12 and at week 24.
The Dermatology Quality of Life Index (DQLI). Each question is scored from 0 (absence) to 3 (intense problem)

| Question | Score |
|---|---|
| 1. How itchy, sore, painful or stinging has your skin condition been? | |
| 2. How embarrassed or self-conscious have you been because of your skin? | |
| 3. How much has your skin interfered with you going shopping or looking after your home or garden? | |
| 4. How much has your skin influenced the clothes you wear? | |
| 5. How much has your skin affected your social or leisure activities? | |
| 6. How much has your skin made it difficult for you to do any sport? | |
| 7. Has your skin prevented you from working or studying? | |
| 8. How much has your skin created problems with your partner or any of your close friends or relatives? | |
| 9. How much has your skin caused any sexual difficulties? | |
| 10. How much of a problem has the treatment for your skin been? | |

The investigators counted the following from each individually affected area and took a photo of that area: the number of fistulas; the number of nodules or abscesses; the number of scars; their impression about the degree of inflammation scored from 0 to 3 as follows: 0, absent, 1, mild; 2, moderate; 3, intense; the two largest dimensions of each lesion in mm Based on the above the following two scores were assessed at each visit: Hidradenitis Suppurativa Clinical Response (HiSCR) score and Physicians' Global Assessment (PGA) score. For HiSCR, patients were defined as achievers or non-achievers. The probability of achieving a positive HiSCR score was starting from the second visit and it was defined as a $\geq 50\%$ reduction in inflammatory lesion count (sum of abscesses and inflammatory nodules), and no increase in abscesses or draining fistulas in HS when compared with baseline. For PGA, this score was classified as: a) clear when the total number of abscesses is 0, the total number of draining fistulas is 0, the total number of inflammatory nodules is 0 and the total number of non-inflammatory nodules is 0; b) minimal when the total number of abscesses is 0, the total number of draining fistulas is 0, the total number of inflammatory nodules is 0 and there is presence of non-inflammatory nodules; c) mild when the total number of abscesses is 0, the total number of draining fistulas is 0, and the total number of inflammatory nodules is 1-4 or when there is presence of one abscess or draining fistula and absence of any inflammatory nodule; d) moderate when the total number of abscesses is 0, the total number of draining fistulas is 0 and the total number of inflammatory nodules is up to 5 or when there is presence of one abscess or draining fistula and up to one inflammatory nodule; e) severe when the total number of abscesses or draining fistulas is 2-5 and the total number of inflammatory nodules is 5-10; and f) very severe when there are more than 5 abscesses or draining fistulae.

Disease activity. This is defined as the sum of scores of all affected areas of each patient. Each area was evaluated by the following formula: (multiplication of the two largest diameters in each affected area in mm)×(the degree of inflammation of each lesion).

The modified Sartorius score. This is the sum of separate scoring for each affected area using the data recorded as follows: a) 3 points per anatomical region involved; b) 6 points for each fistula and 1 point for each nodule or abscess; c) 1 point when the longest distance between two relevant lesions in each affected area is <5 cm; 3 points when it is 5-10 cm; and 9 points when it is >10 cm; and d) 9 points when there is no clear separation of lesions from adjacent normal skin and 0 points when there is.

The efficacy of MABp1 in patients with moderate to severe HS by HiSCR scoring was assessed by the difference of achievement of positive HiSCR score between the treatment group and the comparator placebo group at week 12. The long-term efficacy of MABp1 in patients with moderate to severe HS by positive HiSCR scoring was assessed by the difference of achievement of HiSCR score between the treatment group and the comparator placebo group at week 24. Analysis was done separately for patients with previous failure or relapse under adalimumab and for patients without previous adalimumab treatment. The short- and long-term efficacy of MABp1 in patients with moderate to severe HS was assessed by the comparisons of all used scoring systems (HiSCR, PGA, DLQI, disease activity, VAS for disease, VAS for pain and modified Sartorius score) on all study visits. Analysis was also done separately for patients with previous failure or relapse under adalimumab and for patients without previous adalimumab treatment. The effect of MAbp1 on the time to new exacerbation was assessed by comparing the time to new exacerbation from week 0 between the two groups of treatment. Analysis was done separately for patients with previous failure or relapse under adalimumab and for patients without previous adalimumab treatment. Comparisons of HiSCR between the two study groups was done by the Fischer's exact test. Comparisons of severity score for each study visits were done by non-parametric statistics. Comparison of the time to new exacerbation between the two groups was done by the log-rank test.

Results. FIGS. 1-12 show the results of the study. Patients treated with MABp1 achieved a significantly greater rate of positive HiSCR scores than comparators. Treatment with MABp1 was associated with significant: increased positive HiSCR scoring at week 24; decreased total AN count (more pronounced in patients without previous anti-TNF exposure); decreased VAS for the disease; prolongation of the time to new exacerbations in patients without previous anti-TNF exposure; and significant decrease of US depth of total body lesions (more pronounced in patients without previous anti-TNF failure).

Example 2

The topline results from an investigator sponsored randomized Phase 2 study evaluating MABp1 as a treatment for Hidradenitis Suppurativa (HS) showed that study met its primary endpoint, demonstrating significant improvement of HS patients compared to control after 12 weeks of therapy (response rate of 60% vs 10%, respectively (p=0.035)).

The 20 patient double-blind, placebo-controlled study was designed to evaluate the safety and efficacy of MABp1, a True Human™ antibody targeting interleukin-1 alpha (IL-1α), in patients with HS not eligible for anti-TNFα therapy. Patients were randomized 1:1 to receive either MABp1 or placebo every 2 weeks for 12 weeks. Patients in the study underwent primary assessment of efficacy using Hidradenitis Suppurativa Clinical Response (HiSCR) scores at 12 weeks, continued by a follow up phase to assess time to relapse after an additional 12 weeks without therapy. Efficacy measures include assessment of HiSCR scores, a validated method for evaluating efficacy in HS patients, as well as quality of life assessment and ultrasonographic evaluation.

Figure 2:
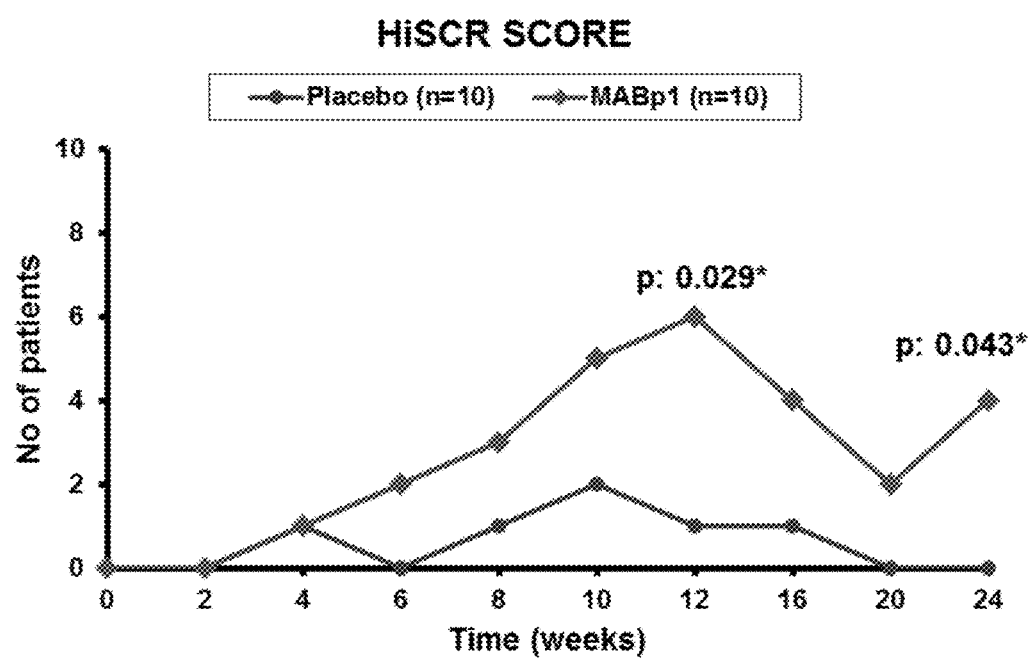
FIG. 2 is a graph showing that the clinical efficacy of MABp1 was maintained until week 24 (i.e., 12 weeks after treatment was stopped), where no patients treated with placebo had a positive HiSCR score (0%) compared to four out of 10 patients (40%) treated with MABp1.
Figure 3:
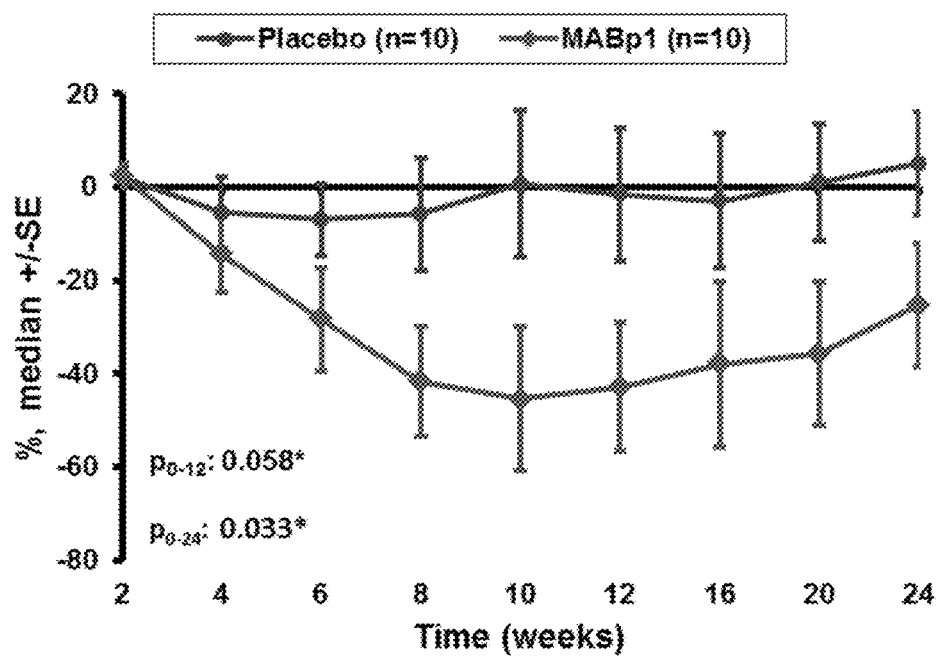
FIG. 3 is a graph showing the percent change of the total AN (sum of inflammatory nodules and abscesses) count in all patients over the first 24 weeks after the start of treatment with MABp1 or placebo.
Figure 4:
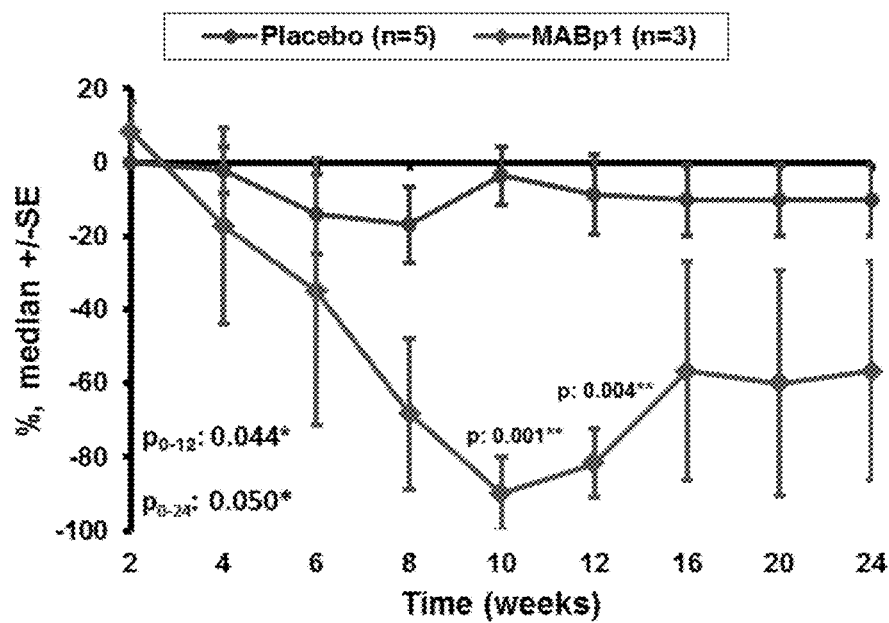
FIG. 4 is a graph showing the percent change of the total AN count in patients without previous exposure to anti-TNFα over the first 24 weeks after the start of treatment with MABp1 or placebo.
Figure 5:
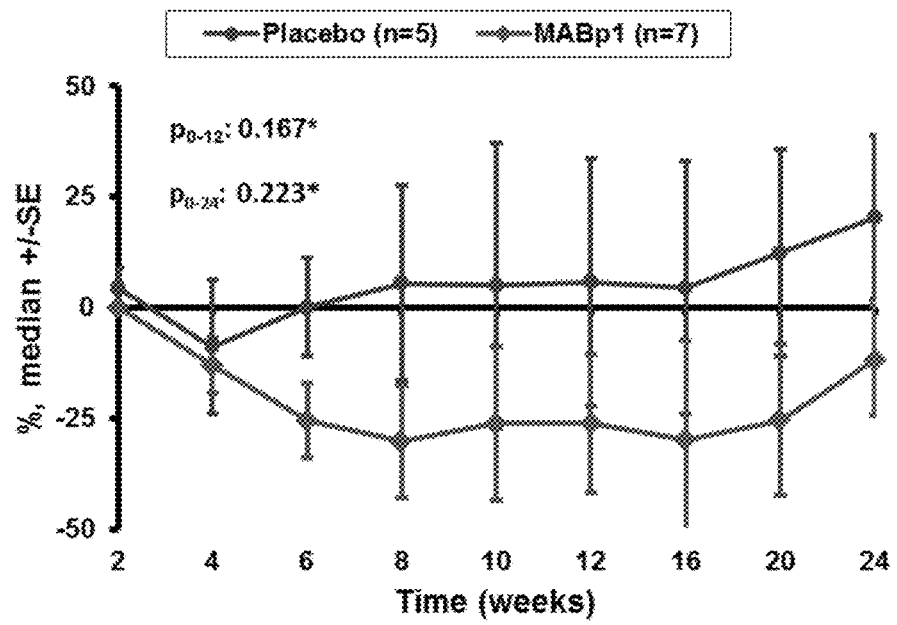
FIG. 5 is a graph showing the percent change of the total AN count in patients with previous anti-TNFα treatment failure over the first 24 weeks after the start of treatment with MABp1 or placebo.
Figure 6:
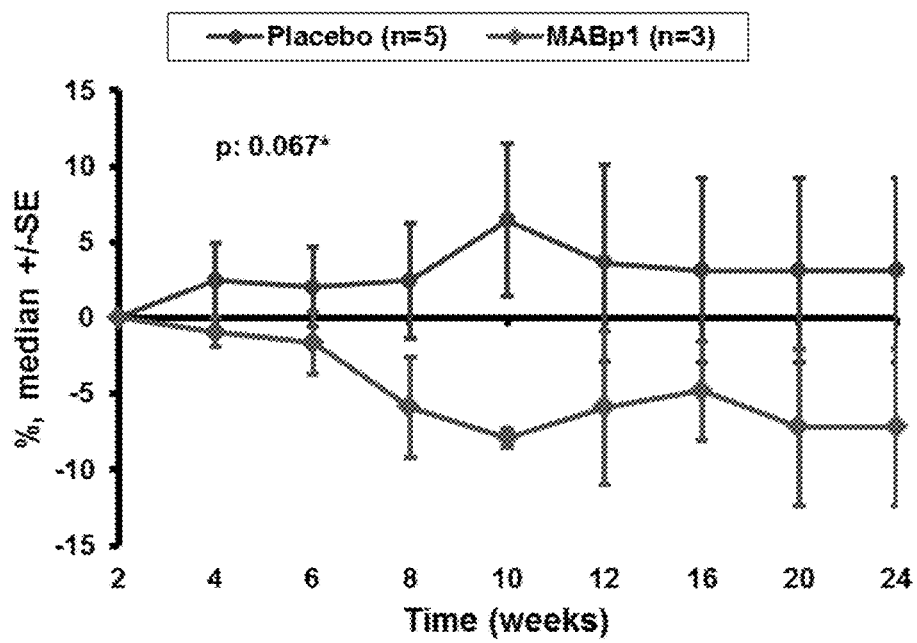
FIG. 6 is a graph showing the percent change in disease activity in patients without previous exposure to anti-TNFα over the first 24 weeks after the start of treatment with MABp1 or placebo.
Figure 7:
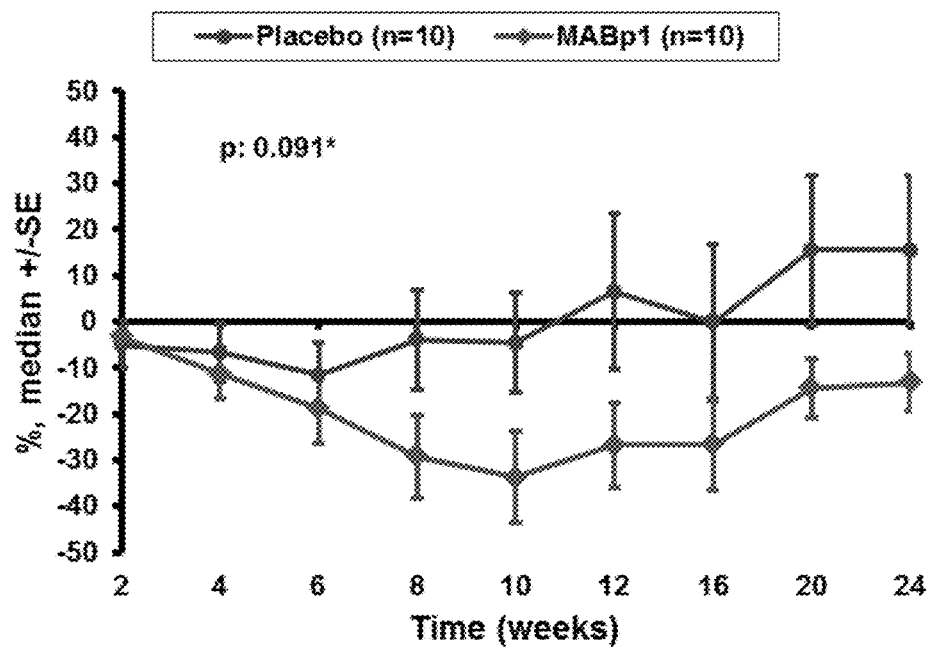
FIG. 7 is a graph showing the percent change in visual analogue scale (VAS) in all patients over the first 24 weeks after the start of treatment with MABp1 or placebo.
Figure 8:
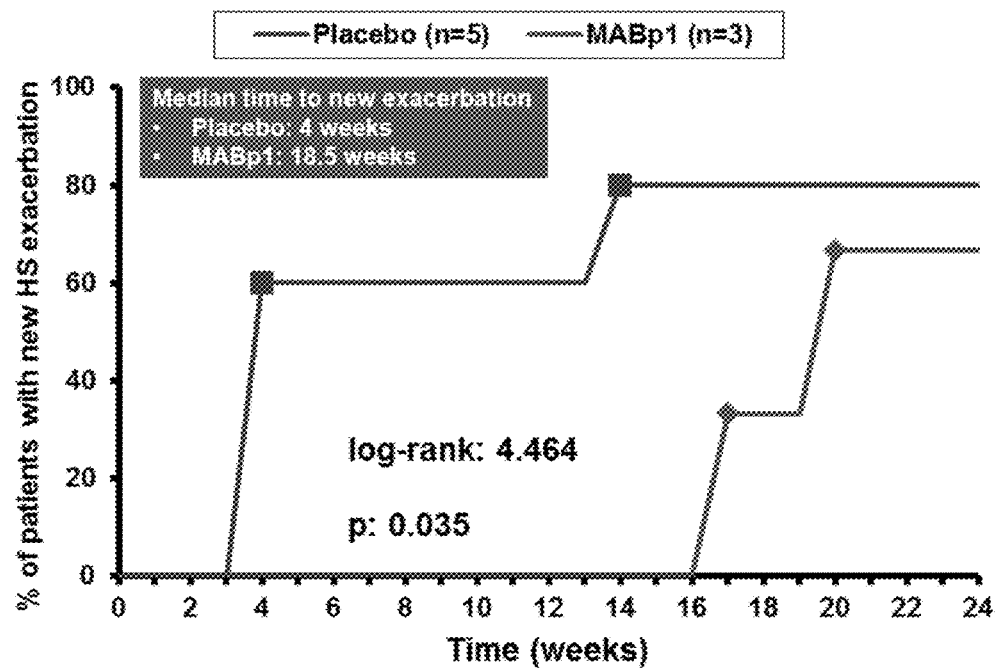
FIG. 8 is a graph showing the median time to new exacerbations in patients without previous exposure to anti-TNFα over the first 24 weeks after the start of treatment with MABp1 or placebo.
Figure 9:
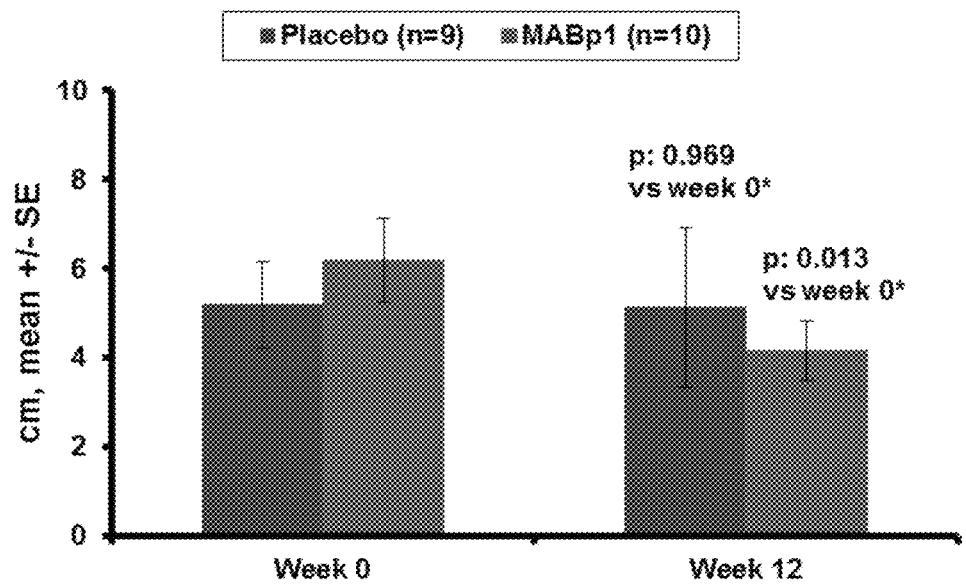
FIG. 9 is a graph showing the change in lesion depth in all patients after 12 weeks from the start of treatment with MABp1 or placebo.
Figure 10:
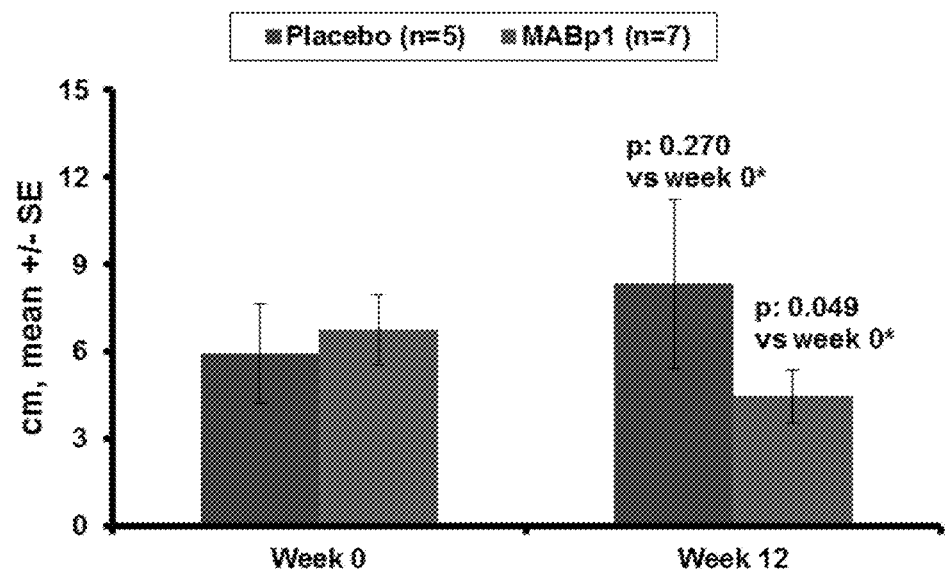
FIG. 10 is a graph showing the change in lesion depth in patients with previous anti-TNFα treatment failure after 12 weeks from the start of treatment with MABp1 or placebo.
Figure 11:
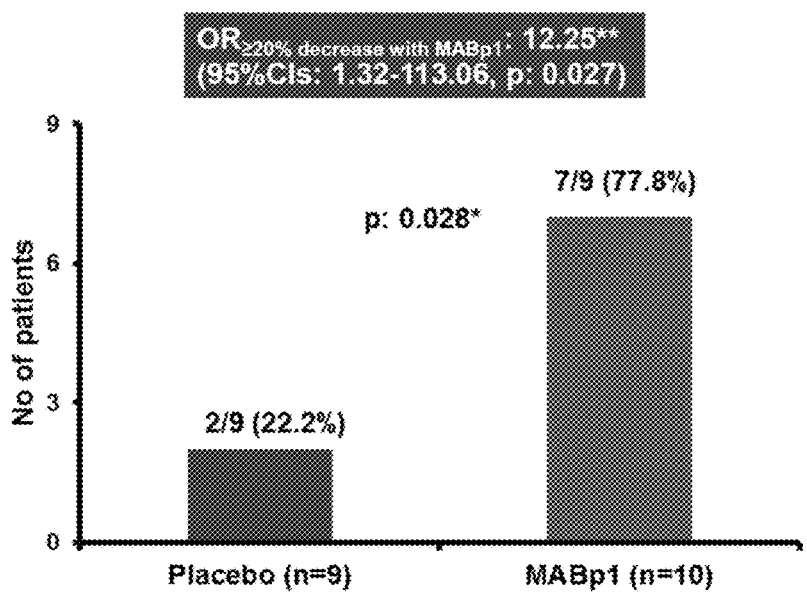
FIG. 11 is a graph showing the number of patients having at least a 20% reduction in lesion depth in patients treated with MABp1 or placebo.
Figure 12:
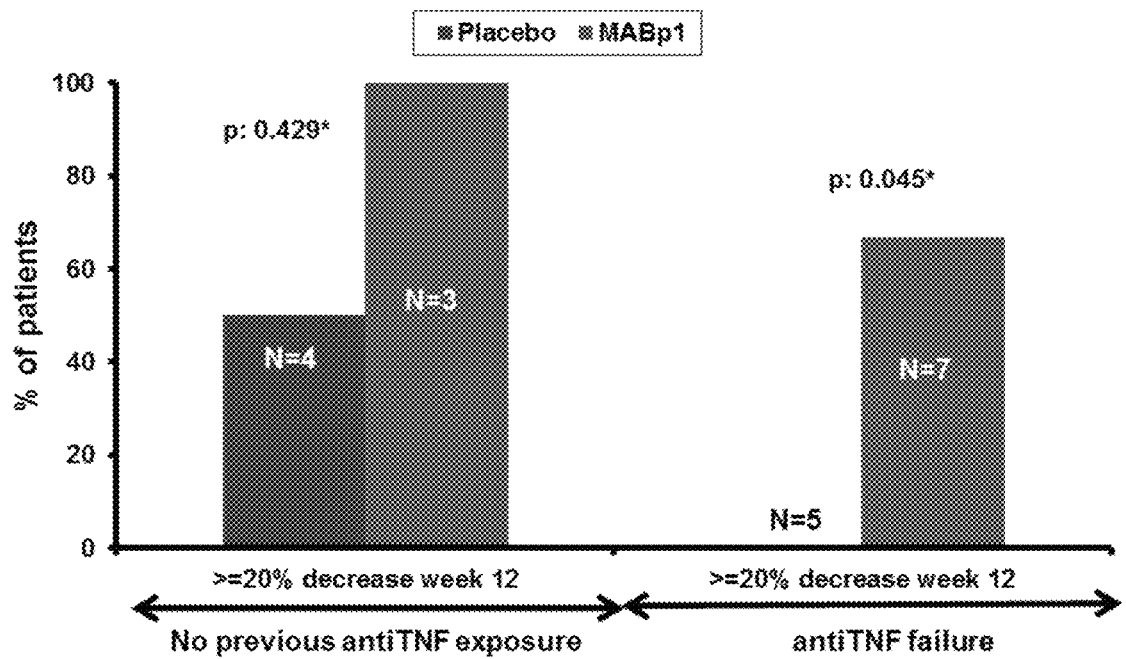
FIG. 12 is a graph showing the number of patients having at least a 20% reduction in lesion depth in patients treated with MABp1 or placebo, wherein the patient populations were (i) those without previous exposure to anti-TNFα and (ii) those with previous anti-TNFα treatment failure.

Sixty percent of patients allocated to treatment with MABp1 achieved positive HiSCR at week 12 compared to 10% of the placebo group (FIG. 1). The odds ratio (OR) for positive HiSCR under MABp1 was 13.50 (95% confidence intervals: 1.19-152.51; p=0.035). The total AN count which is the basic component of the HiSCR score was decreased over the first 12 weeks under treatment (FIG. 3). The clinical efficacy of MABp1 was maintained until week 24, i.e., 12 weeks after treatment was stopped. At that time point, as shown in FIG. 2, no patients treated with placebo had a positive HiSCR score (0%) compared to four out of 10 patients (40%) treated with MABp1. Treatment with MABp1 was also accompanied by better patient-reported outcomes. Decrease of the visual analogue scale (VAS) was found in 30% (three out of 10) and in 70% (seven out of 10) allocated to placebo and MABp1 respectively. Sub-analysis showed that this was 40% (two out of five) and 33.3% (one out of three) respectively among anti-TNFs naïve patients and 20% (one out of five) and 85.7% (six out of seven) among patients failing previous treatment with anti-TNFs. The median time to the first HS exacerbation was seven weeks in the placebo group and 11 weeks in the MABp1 group. This time did not differ significantly between groups (log-rank: 1.98, p=0.159). However, when sub-analysis was done among anti-TNFs naïve patients, it was found that the median time until a new HS exacerbation was 4 weeks with placebo treatment and 18.5 weeks with MABp1 treatment (log-rank test: 4.46; p=0.035; see FIG. 8). A decrease in disease activity was found in all patients treated with MABp1 and who achieved positive HiSCR at weeks 12 and 24. A decrease of at least two of the assessed scores i.e. Physicians' Global Assessment (PGA), disease activity, modified Sartorius score, VAS for pain, and dermatology life quality index (DLQI) at week 12 was found in 40% of patients allocated to placebo and 80% of patients allocated to MABp1 (80%) (OR=14.50; 95% confidence intervals: 0.96-218.99; p=0.054). Sub-analysis showed that this was 60% (three out of five) and 100% (three out of three) respectively among anti-TNFs naïve patients and 20% (one out of five) and 71.4% (five out of seven) among patients failing previous treatment with anti-TNFs. Significant changes in variables for skin ultrasound included total lesion vascularity and total lesion depth, which is the sum of the grading of vascularity and the sum of the greatest depth of all involved skin areas, respectively. Both variables were decreased after treatment with MABp1 (FIGS. 9-12). More than 20% decrease of total lesion depth was selected as a cut-off point, and it was found in 22.2% of patients allocated to placebo compared to 77.8% of patients treated with MABp1 (OR=12.25; 95% confidence intervals 1.33-113.06; p=0.027). The effect was pronounced among patients who have failed previous anti-TNFs (FIG. 10). Significant improvement in the elasticity of the affected areas was also noted.

Serum IL-1α was below the lower limit of detection in the sera sampled from all patients both before and at the end of blind treatment. Pus was sampled before treatment from six patients allocated to placebo and seven patients allocated to MABp1. Mean±SE concentrations of IL-1α were 697.2±440.4 pg/ml and 772.0±221.7 pg/ml respectively (p=0.412 by the Mann-Whitney U test). Treatment with MABp1 was accompanied by decrease of serum IL-8. More than 30% decrease of IL-8 on week 12 was selected as a cut-off point. The OR for this cut-off point by MABp1 was 13.50 (95% confidence intervals: 1.19-152.51; p=0.035). This was consistent with change in levels of IL-8 produced from whole blood stimulated with heat-killed *Staphylococcus aureus*, which was significantly lower among patients treated with MABp1 than patients treated with placebo. The capacities of whole blood to produce both IL-1α and human β-defensin (hBD)-2 were positively associated among placebo-treated patients. Among the same patients, the capacity for hBD-2 production was negatively correlated with the change of the skin depth of the lesions at ultrasound. These correlations ceased to exist among MABp1-treated patients, which suggested an hBD-2-associated mode of action of MABp1 in HS that was mediated through the inhibition of IL-1α.

Safety—no study drug related adverse events or serious adverse events occurred in the study.

Analysis of the data using the iHS4 score for all 20 patients who were randomized to receive either placebo or MABp1 therapy in the Phase 2 double-blind study was performed. At least a 30% decrease of the iHS4 score from the baseline at week 12 was associated with 100% sensitivity for positive HiSCR score (the efficacy measure used in the phase 2 study). This change was found in one (10%) and in four (40%) patients allocated to placebo and MABp1, respectively (p=0.046).

Patients that had originally been allocated to placebo in the Phase 2 study were allowed to receive treatment with the MABp1 antibody therapy in a so called open label extension (OLE) study. Seven of 10 patients that had originally received placebo were treated with MABp1 for 12 weeks. Main endpoints used in the OLE included safety and HiSCR score at the end of the 12 week treatment. At the conclusion of the double-blinded study, only one patient (1 of 10, or 10%) receiving placebo had achieved HiSCR. During the OLE, five patients (5 of 7, or 71.4%) achieved the HiSCR response (p=0.035). There was a total of 24 HS exacerbations during the blinded portion of the study compared to just 1 exacerbation during the OLE phase.

"The overall response rate observed in the data is, in my opinion, groundbreaking for the treatment of HS," Dr.

Giamarellos-Bourboulis commented, "I am truly encouraged by these results and very much look forward to the future use of MABp1 as a treatment for this devastating condition."

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating hidradenitis suppurativa in a human subject having lesions associated with hidradenitis suppurativa, the method comprising the step of administering to the subject a pharmaceutical composition comprising a pharmaceutically acceptable carrier and an amount of an anti-interleukin-1α antibody having all of the complementarity determining regions (CDRs) of MABp1 effective to treat a symptom of hidradenitis suppurativa in the subject, wherein the pharmaceutical composition is administered at a regimen such that the subject receives 1-20 mg/kg body weight of the anti-interleukin-1α antibody every 0.5-4 weeks.

2. The method of claim 1, wherein the anti-IL-1α antibody is a monoclonal antibody.

3. The method of claim 2, wherein the monoclonal antibody is an IgG1.

4. The method of claim 3, wherein the monoclonal antibody is MABp1.

5. The method of claim 1, wherein the subject's Hidradenitis Suppurativa Clinical Response (HiSCR) score is improved after administration of the pharmaceutical composition.

6. The method of claim 1, wherein the median size of the subject's hidradenitis suppurativa lesions is reduced after administration of the pharmaceutical composition.

7. The method of claim 1, wherein the subject's pain associated with the subject's hidradenitis suppurativa lesions is reduced after administration of the pharmaceutical composition.

8. The method of claim 1, wherein the subject's time to new hidradenitis suppurativa lesions is increased after administration of the pharmaceutical composition.

9. The method of claim 1, wherein the hidradenitis suppurativa in the human subject has failed to resolve after treatment with tumor necrosis factor alpha inhibitors.

10. A method of treating hidradenitis suppurativa in a human subject in need thereof, comprising administering to the subject a therapeutically effective amount of a pharmaceutical composition comprising a pharmaceutically acceptable carrier and MABp1, wherein the subject achieves a positive Hidradenitis Suppurativa Clinical Response (HiSCR) score after administration of the pharmaceutical composition, and the positive HiSCR score is defined as a >50% reduction in inflammatory lesion count of the sum of abscesses and inflammatory nodules and no increase in abscesses or draining fistulas in hidradenitis suppurativa when compared with baseline, wherein the pharmaceutical composition is administered at a regimen such that the subject receives 1-20 mg/kg body weight of the MABp1 every 0.5-4 weeks.

11. The method of claim 10, wherein the median size of the subject's hidradenitis suppurativa lesions is reduced after administration of the pharmaceutical composition.

12. The method of claim 10, wherein the subject's pain associated with the subject's hidradenitis suppurativa lesions is reduced after administration of the pharmaceutical composition.

13. The method of claim 10, wherein the subject's time to new hidradenitis suppurativa lesions is increased after administration of the pharmaceutical composition.

14. The method of claim 10, wherein the hidradenitis suppurativa in the human subject has failed to resolve after treatment with tumor necrosis factor alpha inhibitors.

15. The method of claim 10, further comprising administering to the subject one or more other agents selected from the group consisting of corticosteroids, retinoids, resorcinol, hormones, adalimumab, infliximab and antimicrobials.

16. A method of treating hidradenitis suppurativa in a human subject in need thereof, comprising administering to the subject a therapeutically effective amount of a pharmaceutical composition comprising a pharmaceutically acceptable carrier and MABp1, wherein after administration of the pharmaceutical composition, one or more of the following are achieved:
(1) the subject's Hidradenitis Suppurativa Clinical Response (HiSCR) score is improved;
(2) the median size of the subject's hidradenitis suppurativa lesions is reduced;
(3) the subject's pain associated with the subject's hidradenitis suppurativa lesions is reduced; or
(4) the subject's time to new hidradenitis suppurativa lesions is increased;
wherein the pharmaceutical composition is administered at a regimen such that the subject receives 1-20 mg/kg body weight of the MABp1 every 0.5-4 weeks.

17. The method of claim 16, wherein the hidradenitis suppurativa in the human subject has failed to resolve after treatment with tumor necrosis factor alpha inhibitors.

18. The method of claim 16, further comprising administering to the subject one or more other agents selected from the group consisting of corticosteroids, retinoids, resorcinol, hormones, adalimumab, infliximab and antimicrobials.

* * * * *